US006664257B2

(12) United States Patent
Yatvin et al.

(10) Patent No.: US 6,664,257 B2
(45) Date of Patent: Dec. 16, 2003

(54) ANTI-MYCOBACTERIAL COMPOUNDS

(75) Inventors: Milton B. Yatvin, Portland, OR (US); Richard L. Pederson, San Gabriel, CA (US)

(73) Assignee: EnzRel Inc., Portland, OR (US)

( * ) Notice: Subject to any disclaimer, the term of this patent is extended or adjusted under 35 U.S.C. 154(b) by 3 days.

(21) Appl. No.: 09/993,974

(22) Filed: Nov. 5, 2001

(65) Prior Publication Data

US 2003/0100569 A1 May 29, 2003

(51) Int. Cl.$^7$ ........................ A61K 31/50; A61K 31/495
(52) U.S. Cl. ...................................... 514/247; 514/252.1
(58) Field of Search ............................... 514/247, 252.1

(56) References Cited

U.S. PATENT DOCUMENTS

| | | | | |
|---|---|---|---|---|
| 3,108,099 A | * | 10/1963 | Felder et al. | ............ 260/247.2 |
| 6,063,759 A | | 5/2000 | Yatvin et al. | |
| 6,399,607 B1 | * | 6/2002 | Welch et al. | ................ 514/247 |

OTHER PUBLICATIONS

Miniyar et al., "Pyrazinoic acid hydrazide derivatives: synthesis and antimycobacterial activities", Indian Journal of Heterocyclic Chemistry (1999), 9(2), pp. 155–156.*
Adachi et al., "Cloning and Expression of Dipeptidase from Acinetobacter calcoaceticus ATCC 23055", J. Biochem. 118, 555–561 (1995).
Barry et al., "Pathogenicity and Immunogenicity of *Listeria monocytogenes* Small–Plaque Mutants Defective for Intracellular Growth and Cell–to–Cell Spread" 1992, Infect. Immun. 60:1625–1632.
Cheng & Thiebert, 2000, Antimicrob. Agents Chemother. 43:537–542.
Denis et al., "Killing of *Mycobacterium smegmatis* by Macrophages from Genetically Susceptible and Resistant Mice", 1990, J. Leuk. Biol. 47:25–29.
Drevets and Campbell "Roles of Complement and Complement Receptor Type 3 in Phagocytosis of *Listeria monocytogenes* by Inflammatory Mouse Peritoneal Macrophages", 1991, Infect. Immun. 59:517–523.
Drevets et al., "Listericidal and nonlistericidal mouse macrophasges differ in complement receptor type 3–mediated phagocytosis of *L. monocytogenes* and in preventing escape of the bacteria into the cytoplasm", 1992, J. Leuk. Biol. 52:70–79.
Heifets et al., "Does Pyrazinoic Acid as an Active Moiety of Pyrazinamide Have Specific Activity against *Mycobacterium tuberculosis*", 1989, Antimcrob. Agents, Chemother. 33:1232–1234.
Hoashi et al., 1999, Kekkaku 74:441–445.
Hou et al., "Molecular Characterization of pncA gene mutations in *Mycobacterium tuberculosis* clinical isolates from China", 2000, Epidemiol. Infect. 124:227–232.
Kabat et al., 1988, Chem. Pharm. Bull. 36:634–640.

Kushner et al., Experimental Chemotherapy of Tuberculosis. II. The Synthesis of Pyrazinamides and Related Copounds: 1952, J. Amer. Chem. Soc. 74:3617–3621.
MacKall et al., "A Mild Procedure for the Rapid Release of Cytoplasmic Enzymes from Cultured Animal Cells", 1979, Analyt. Biochem. 95:270–274.
Martilla et al., "pncA Mutations in Pyrazinamide–Resistant *Mycobacterium tubersulosis* Isolated fromNorthwestern Russia", 1999, Antimicrob. Agents Chemother. 43:1764–1766.
Mestdagh et al., "Relationship between Pyrazinamide Resistance, Loss of Pyrazinamidase Activity, and Mutations in the pncA Locus in Multidrug–Resistant Clinical Isolates of *Mycobacterium tuberculosis*", 1999, Antimicrob. Agents Chemother. 43:2317–2319.
Miniyar and Bhat, "Pyrazinoic Acid Hydrazide Derivatives: Synthesis and Antimycobacterial Activities", Indian Journal of Heterocyclic Chemistry, vol. 9, Oct.–Dec. 1999, pp. 155–156.
Nibbering et al., "Bacteriostatic Activity of BCG/PPD–Activated Macrophages Against *Mycobacterium fortuitum* Does Not Involve Reactive Nitrogen or Oxygen Intermediates", 1994, Scand. J. Immunol. 40:187.
Peck, "A One–Plate Assay for Macrophage Bactericidal Activity", 1985, J. Immunol. Methods 82:131–140.
Radzioch et al., "Genetic Resistance/Susceptibility to Mycobacteria: Phenotypic Expression in Bone Marrow Derived Macrophage Lines", 1991, J. Leuk. Biol. 50:263.
Raynaud et al., "Mechanisms of pyrazinamide resistance in mycobacteria: importance of lack of uptake in addition to lack of pyrazinamidase activity", 1999, Microbiol. 145:1359–1367.
Shetty et al., "Occurrence of $\gamma$–Glutamyl Transpeptidase Activity in Several Mycobacteria Including *Mycobacterium leprae*", 1981, Intl. J. Lepr. Other Mycobact. Dis. 49:49–56.
Sing et al., "Severe Cutaneous *Mycobacterium chelonei* infection following a yellow jacket sting", 1992, Tubercle & Lung Dis. 73:305.
Steven et al., "*Mycobacterium fortuitum* Keratitis. A Comparison of Topical Ciprofloxacin and Amikacin inand Animal Model", 1992, Cornea 11:500.
Van Furth et al., "Mycobacteria and Macrophage Activation" 1990, Res. Microbiol. 141:256.

* cited by examiner

Primary Examiner—Kevin E. Weddington
(74) Attorney, Agent, or Firm—McDonnell Boehnen Hulbert & Berghoff

(57) ABSTRACT

This invention provides compositions of matter, pharmaceutical compounds, methods of synthesizing such compounds and methods for using such compounds to treat animals infected with a pathogenic mycobacterium. The invention specifically provides compositions and pharmaceutical compositions thereof for the treatment of tuberculosis and other Mycobacterium-caused diseases.

16 Claims, No Drawings

ANTI-MYCOBACTERIAL COMPOUNDS

BACKGROUND OF THE INVENTION

1. Field of the Invention

This invention relates to anti-mycobacterial compounds, pharmaceutical compositions thereof, methods of synthesizing such compounds and methods for using such compounds to treat animals infected with a pathogenic microorganisms, specifically mycobacteria. The invention relates in particular to compositions of matter and pharmaceutical compositions thereof for the treatment of tuberculosis and other Mycobacterium-caused diseases.

2. Background of the Related Art

Tuberculosis is a human disease caused by infection with *Mycobacterium tuberculosis*. This disease typically arises in phagocytic macrophages in the lung after inhalation, where characteristic localized sites of infection (termed tubercules) are formed and comprise sites of further systemic infection. Although previously well-controlled by antibiotics such as pyrazinamide, the development of drug-resistance by the infectious agent, and the increased numbers of immune-compromised individuals being affected by the AIDS crisis has created a near epidemic of tuberculosis cases worldwide. In 1997, the World Health Organization reported tuberculosis to be the world's top infectious killer.

About one-third of new tuberculosis cases are resistant to the current drug-treatment regimens, and estimates are that drug-resistant tuberculosis accounts for between 2% and 14% of total tuberculosis cases worldwide. As tuberculosis is spread by air-borne droplets from coughing by infected individuals, and its spread being further facilitated in crowded environments such as cities, there is a great potential for a precipitous increase in tuberculosis infections, which will not be easily controlled by conventional medicinal intervention, such as pyrazinamide administration. Lethal strains of tuberculosis have the potential for rapid spread, since only about one in ten patients receives the medical treatment necessary to contain and successfully treat the disease. Thus, there exists in this art a need to develop new and better treatments for tuberculosis, particularly tuberculosis infections resistant to traditional antibiotic treatments.

There is also a need in the art for more effective anti-tuberculosis drugs to which *M. tuberculosis* is not resistant and, most advantageously, drugs having a low resistance development potential.

In addition, there are a number of other human and animal diseases caused by mycobacteria, including for example leprosy (Hansen's disease), lymphadenitis, a variety of pulmonary and skin diseases, and wound infection. Although less prevalent, each of these diseases is associated with morbidity, mortality and economic costs such as lost production time and the cost of medical treatment. Resistance to drugs used heretofore to control and treat such diseases is also a current problem, thus raising a further need in this art for more effective drugs against many different Mycobacterium species.

SUMMARY OF THE INVENTION

The present invention is directed to improved antibiotic compounds, specifically pharmaceutical compositions thereof, and methods for producing and administering such pharmaceutical compositions, for treatment of diseases having a Mycobacterium etiology. In particular, the invention is directed towards delivery of antimycobacterial compounds, drugs and agents specific for treatment of tuberculosis and other Mycobacterium-caused diseases in humans.

The invention provides improved antimycobacterial drugs that are derivatives of pyrazinamide. Pyrazinamide is a so-called "first-line" anti-tubercular drug that has been widely used in humans, and is the drug of choice in countries such as China and the republics of the former Soviet Union (Hou et al., 2000, *Epidemiol. Infect.* 124: 227–232; Hoashi et al., 1999, *Kekkaku* 74: 441–445; Martilla et al., 1999, *Antimicrob. Agents Chemother.* 43: 1764–1766). Pyrazinamide is the prodrug form of the biologically active drug pyrazinoic acid, which has been shown to have specific antibiotic activity against *M. tuberculosis* (Heifets et al., 1989, *Antimicrob. Agents Chemother.* 33: 1232–1234). However, pyrazinoic acid cannot be administered directly because it is a charged species at physiological pH and cannot cross the *M. tuberculosis* cell membrane (Raynaud et al., 1999, *Microbiol.* 145: 1359–1367). Pyrazinamide is converted in the mycobacterium to the active form by an amidase, but the precise mechanism of antimycobacterial activity is unknown. Neither the prodrug nor active drug form is toxic to humans in therapeutically-effective dosages.

The effectiveness of pyrazinamide has been reduced by the development of resistant strains of *M. tuberculosis* (Raynaud et al., ibid.; Mestdagh et al., 1999, *Antimicrob. Agents Chemother.* 43: 2317–2319). A significant source of pyrazinamide resistance is a mutation in a mycobacterial gene, pncA (Cheng & Thiebert, 2000, *Antimicrob. Agents Chemother.* 43: 537–542), responsible for converting the drug from prodrug (pyrazinamide, Structure I below) to active drug (pyrazinoic acid, Structure II below) (Sun & Zhang, 1999; Cheng & Thiebert, 2000, *Antimicrob. Agents Chemother.* 44: 528–532). The invention provides alternative embodiments of pyrazinamides that are secondary amides (generic Structure III below). These compounds provide alternative routes for pyrazinamide activation in *M. tuberculosis* that bypass the mutant pncA gene, by activation through mycobacterial aminohydrolases, most preferably one or a multiplicity of non-specific aminohydrolases.

Structure I

Pyrazinamide

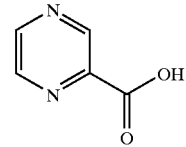

Structure II

Pyrazinoic acid

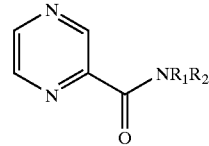

Structure III

The invention thus provides as a composition of matter pyrazinamide derivatives having generic structure III, wherein $R_1$ or $R_2$ can each independently be H, lower alkyl ($C_1$ to $C_{10}$), alkoxy, lower cycloalkyl including bridgehead compounds and — and O— cyclized bridgehead compounds such as bicyclo[2.2.2]octane and bicyclo[2.2.1]heptane, cycloalkoxy, lower alkyl carboxy including fatty acids, $C_1$ to $C_{10}$ alkenyl comprising 1 to 3 alkenyl (C=C) moieties, aryl or substituted aryl, benzyl or $C_1$ to $C_{10}$ arylalkyl or substituted arylalkyl, heterocyclic aryl or arylalkyl, naphthyl, alkylamino, halogenated derivatives thereof, or D- or L-amino acids or di- or tripeptides comprised of any mixture thereof, provided that at least one of $R_1$ or $R_2$ are not H. In preferred embodiments, $R_1$ or $R_2$ is methyl, ethyl, methoxy, ethoxy, carboxymethyl, β-lactam, or D- or L-amino acids, or di- or tripeptides. It is expected that resistance is less likely to be developed against these drugs.

Particularly preferred targets of the pharmaceutical compositions of the invention are phagocytic cells, preferably macrophages and phagocytic neutrophiles and most preferably macrophages, mononuclear cells and phagocytic neutrophiles from lung tissue that are infected with M. tuberculosis, M. africanum, M. bovis or any other microorganism that causes tuberculosis in an animal, most preferably a human. Also preferred targets are cells infected with M. leprae, M. avium, M. intracellulare, M. scrofulaceum, M. kansasii, M. xenopi, M. marinum, M. ulcerans, M. fortuitum and M. chelonae.

The anti-mycobacterial compounds of the invention are advantageous because, inter alia, the compounds are inhibitors of a target enzyme specific for mycobacterial cells. Inhibition of this enzyme is unlikely to be disadvantageous to infected animals, since neither the prodrug (pyrazimamide) or the active drug (pyrazinoic acid) is toxic to human or animal cells at therapeutic dosages. In addition, the anti-mycobacterial compounds and pharmaceutical compositions thereof are provided in a form that is activated once the drug has passed into the mycobacterial cell in a human or animal cell, most preferably phagocytic cells, infected to Mycobacteria species and thus should not be generally available in mammalian cells in vivo.

The invention provides a method of killing a microorganism infecting a mammalian cell, preferably a phagocytic mammalian cell. This method comprises contacting an infected phagocytic mammalian cell with the compositions of matter or pharmaceutical compositions of the invention in vivo or in vitro. The invention also provides methods for treating microbial infections in an animal, most preferably a human wherein the infecting microbe is present inside a phagocytic cell in the human, the method comprising administering a therapeutically effective amount of the compositions of matter or pharmaceutical compositions of the invention to the human in a pharmaceutically acceptable carrier. Thus, the invention also provides pharmaceutical compositions comprising the compositions of matter of the invention in a pharmaceutically acceptable carrier. In a preferred embodiment, the pharmaceutical composition is formulated in an orally-administered dose. In most preferred embodiments, the infecting microorganism is a tuberculosis-causing microorganism such as M. tuberculosis, M. africanum or M. bovis.

Specific preferred embodiments of the present invention will become evident from the following more detailed description of certain preferred embodiments and the claims.

DETAILED DESCRIPTION OF THE PREFERRED EMBODIMENTS

The present invention provides compositions of matter, pharmaceutical compositions and methods of use thereof for treatment of mycobacterium-associated diseases and disorders in an animal. For the purposes of this invention, the term "mycobacterium" is intended to encompass all pathogenic or disease-causing microorganisms, most preferably tuberculosis-causing microorganisms including but not limited to M. tuberculosis, M. africanum, M bovis, M. leprae, M. avium, M intracellulare, M. scrofulaceum, M. kansasii, M. xenopi, M marinum, M. ulcerans, M. fortuitum and M. chelonae.

The terms "anti-mycobacterial drug, anti-tuberculosis drug or anti-Mycobacterium drug" is intended to encompass any pharmacological agent effective in inhibiting, attenuating, combating or overcoming infection of phagocytic mammalian cells by a tuberculosis-causing or other disease-causing Mycobacterium species microbial pathogen in vivo or in vitro. The compounds of the invention include but are not limited to all varieties of drugs or agents, particularly antibiotic and antimycobacterial drugs, and most preferably anti-tuberculosis drugs and agents, having a cytotoxic or cytostatic effect on mycobacterium growth and proliferation, including but not limited to derivatives of pyrazinoic acid, most preferably secondary amido derivative of pyrazinamide. Preferred embodiments of the specific compounds provided by the invention are shown in FIG. 1.

In preferred embodiments, the pyrazinamide derivatives provided by the invention are secondary amines that are specifically activated in mycobacteria-infected cells by mycobacteria-specific amidases. In alternative embodiments, other bacteria-specific activation is exploited to specifically produce pyrazinoic acid in mycobacterium-infected cells.

In one embodiment, pyrazinoic acid is chemically conjugated to the gamma-glutamyl moiety of gamma-glutamic acid, a variant amino acid linkage between the sidechain (gamma) carboxyl group of glutamic acid and a primary amino group, most preferably of an amino acid. An example of such a linkage is glutathione: γ-glutamyl-cysteinyl-glycine:

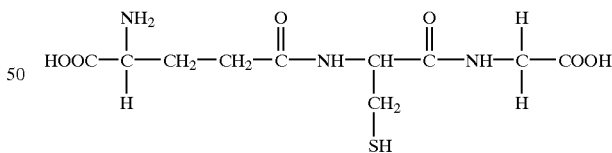

Shetty et al. (1981, Intl. J. Lepr. Other Mycobact. Dis. 49: 49–56 disclosed that several mycobacteria, including M. leprae, express a gamma-glutamyl transpeptidase activity. This activity is capable of transferring the "gamma-glutamyl" group of gamma-glutamyl compounds to several dipeptide and amino acid acceptors. Glycyl D-amino acids were active as acceptors in this report, particularly glycyl-D-alanine and α,ε-diaminopimelic acid, among the amino acids. Since uninfected mammalian cells are incapable of recognizing D-amino acids, these findings provide an alternative route to activating pyrazinoic acid prodrugs in Mycobacterium-infected cells. For example:

Gamma Glutamyl Transpeptidase (GGT)-Dependent Relese Of Pyrazinamide
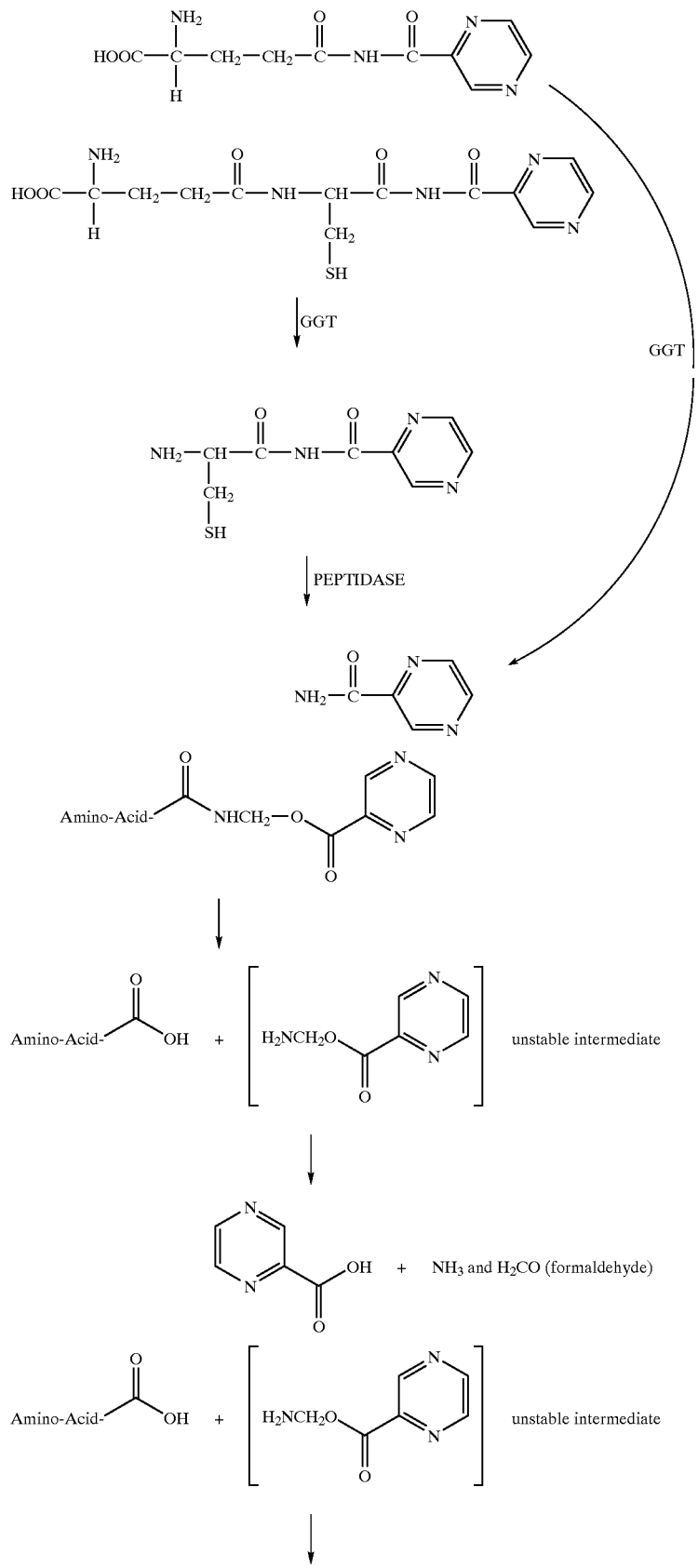

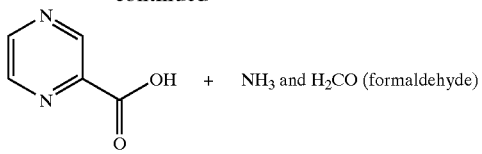

Another alternative method is based on the observation of Adachi et al. (1995, *J. Biochem.* (Tokyo) 118: 555–61) that a dipeptidase having biochemical activity against C-terminal D-amino acids was cloned from *Acinetobacter calcoaceticus* (ATCC 23055). The presence of such an enzymatic activity in Mycobacterium species would permit the following activation scheme using D-amino acid-conjugated pyrazinoic acid:

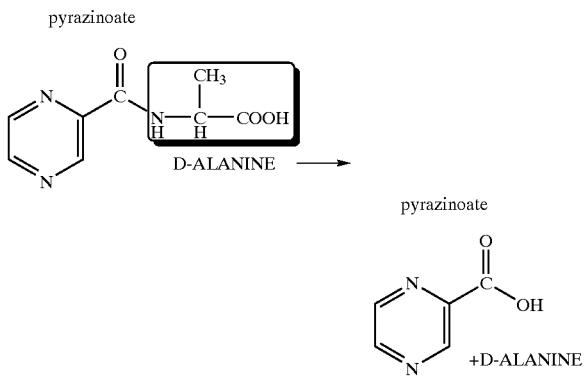

The antimycobacterial, anti-tuberculosis or anti-Mycobacterium compounds, drugs or agents of this invention are useful in inhibiting, attenuating, arresting, combating and overcoming infection of phagocytic mammalian cells by pathogenic microorganisms in vivo and in vitro, particularly tuberculosis-causing species such as *M. tuberculosis, M. africanum* and *M. bovis,* as well as infection by *M. leprae, M. avium, M. intracellulare, M. scrofulaceum, M. kansasii, M. xenopi, M. marinum, M. ulcerans, M. fortuitum* and *M. chelonae.* To this end, the invention provides methods for treating an animal having a disease or disorder caused by one of these microorganisms, wherein the antimycobacterial, anti-tuberculosis or anti-Mycobacterium compounds, drugs or agents of this invention are administered to an animal infected with a pathogenic microorganism that acutely or chronically infects phagocytic mammalian cells. In addition, prophylactic embodiments and uses of the pharmaceutical compounds of the invention are provided, for inoculating vulnerable phagocytic cells prior to or roughly coincident with infection with a pathological or disease-causing microorganism. The antimycobacterial, anti-tuberculosis or anti-Mycobacterium compounds, drugs or agents of this invention for prophylactic or therapeutic uses are administered in a dosage and using a protocol sufficient to have an antimycobacterial effect in the phagocytic cells of the animal.

In addition, pharmaceutical compositions useful in the methods of the invention are also provided, comprising antimycobacterial, anti-tuberculosis or anti-Mycobacterium compounds, drugs or agents of the invention and a pharmaceutically-acceptable carrier, adjuvant or excipient. Routes of administration include oral, ocular, buccal, intranasal, intravenous, intramuscular, parenteral, transdermal, and rectal. In particularly preferred embodiments, the pharmaceutical compositions of the invention are provided in an orally-administered dosage form, including formulations, excipients, binding agents and other features of tablets and other oral dosage forms known in the art. In additional preferred embodiments, the pharmaceutical compositions are provided as an aerosol or other easily-volatilized form, for delivery for example to the lung as provided by conventional inhalers and other pulmonary drug delivery devices and vehicles. Appropriate formulations and pharmaceutical compositions of the antimycobacterial compounds of the invention will be apparent and within the skill of one of ordinary skill in this art to advantageously prepare in view of the instant disclosure.

Pharmaceutical compositions for use in accordance with the present invention thus can be formulated in conventional manner using one or more physiologically acceptable carriers comprising excipients and auxiliaries that facilitate processing of the active conjugates into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0–4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

For injection, the conjugates of the invention can be formulated in appropriate aqueous solutions, such as physiologically compatible buffers such as Hanks' solution, Ringer's solution, or physiological saline buffer. For transmucosal and transcutaneous administration, penetrants appropriate to the barrier to be permeated are used in the formulation. Such penetrants are generally known in the art.

For oral administration, the conjugates can be formulated readily by combining the active conjugates with pharmaceutically acceptable carriers well known in the art. Such carriers enable the conjugates of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active conjugates can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the conjugates for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The conjugates can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active conjugates in water-soluble form. Additionally, suspensions of the active conjugates can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the conjugates to allow for the preparation of highly concentrated solutions. Alternatively, the active ingredient can be in powder form for constitution with a suitable vehicle, e.g., sterile pyrogen-free water, before use. The conjugates can also be formulated in rectal compositions such as suppositories or retention enemas, e.g., containing conventional suppository bases such as cocoa butter or other glycerides.

In addition to the formulations described previously, the conjugates can also be formulated as a depot preparation. Such long acting formulations can be administered by implantation (for example subcutaneously or intramuscularly) or by intramuscular injection. Thus, for example, the conjugates can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic conjugates of the invention is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a solution of 5% dextrose in water solution. This co-solvent system dissolves hydrophobic conjugates well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical conjugates can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the conjugates can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the conjugates for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The antimycobacterial compounds of the invention can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0–4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the antimycobacterial compounds of the present invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the conjugates in a local rather than systemic manner, for example, via injection of the compound directly into a specific tissue, often in a depot or sustained release formulation.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any conjugate species used in the method of the invention, the therapeutically effective dose can be estimated initially in vitro, for example, from cell culture assays, as disclosed herein. For example, a dose can be formulated in animal models to achieve a circulating concentration range that includes the EC50 (effective dose for 50% increase) as determined in cell culture. Such information can be used to more accurately determine useful doses in humans.

It will be understood, however, that the specific dose level for any particular patient will depend upon a variety of factors including the activity of the specific compound employed, the age, body weight, general health, sex, diet, time of administration, route of administration, and rate of excretion, drug combination, the severity of the particular disease undergoing therapy and the judgment of the prescribing physician.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Toxicity and therapeutic efficacy of such conjugates can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Conjugates that exhibit high therapeutic indices are preferred. The data obtained from these cell culture assays and animal studies can be used in formulating a range of dosage for use in humans. The dosage of such conjugates lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in "The Pharmacological Basis of Therapeutics", Ch. 1, p. 1).

The following Examples illustrate certain aspects of the above-described method and advantageous results. The following examples are shown by way of illustration and not by way of limitation.

EXAMPLE 1

Preparing Pyrazinamide Analogs

Pyrazinamide itself is commercially available (Aldrich, Milwaukee, Wis.). Ethylpyrazinamide (Structure IV) and carboxymethylpyrazinamide (Structure V) are prepared from methyl pyrazinoate (Structure VI) essentially according to the method of Kabat et al. (1988, Chem. Pharm. Bull. 36: 634–640) as follows. Ethylpyrazinamide (III below) is prepared by reacting methyl pyrazinoate with ethylamine in methanol at room temperature for 72 hr. Carboxymethylpyrazinamide (IV below) is prepared from methyl pyrazinoate by reaction with methyl glycine in methanol at room temperature, followed by treatment with 0.1M sodium hydroxide and neutralization with a solution of hydrochloric acid, pH 3. The products are purified and characterized by mass spectroscopy and $^1$H- and $^{13}$C-NMR. These reactions are outlined below:

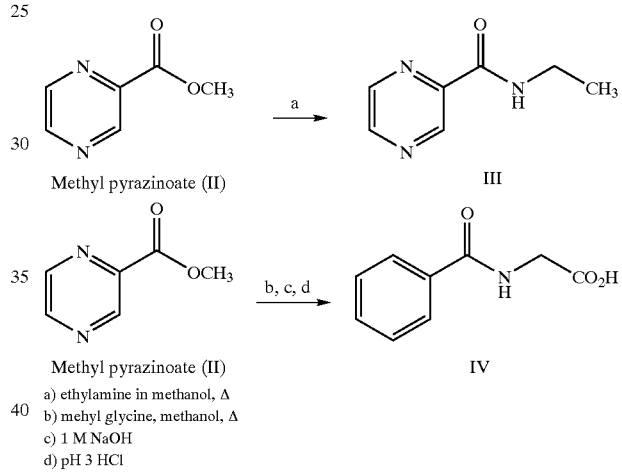

Methyl pyrazinoate (II)    III

Methyl pyrazinoate (II)    IV a) ethylamine in methanol, Δ
b) mehyl glycine, methanol, Δ
c) 1 M NaOH
d) pH 3 HCl Exemplary Synthesis of n-Butyl Pyrazinamde Synthesis of n-butylpyrazinamide is performed as described by Kushner et al. (1952, J. Amer. Chem. Soc. 74: 3617–3621). Briefly, to a 50 mL round bottomed flask containing a magnetic stirbar, was added 5.0 g (36.2 mmol) methyl pyrazinoate and 25 mL of anhydrous ethanol, under an inert atmosphere of argon. Anhydrous n-butyl amine (7.71 g, 108.6 mmol) was added dropwise over 30 min. The mixture was stirred and warmed to room temperature for 24 hr, which was sufficient time for the reaction to go to completion as determined by thin-layer chromatography. The solvent and excess n-butyl amine were removed under high vacuum, leaving 5.83 g (32.5 mmol) of n-butyl pyrazinamde as a viscous syrup. This material was recrystallized to yield 4.53 g of n-butyl pyrazinamde as white crystals.

Structure VI

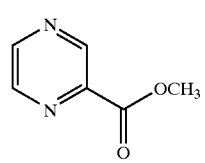

-continued

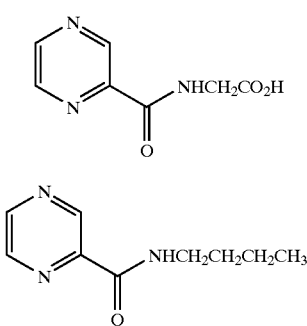

Structure V

Structure VI

EXAMPLE 2

Pyrazinamidase and Aminohydrolase Assays

Because mycobacterial pyrazinamidase is not commercially available, cleavage of the pyrazinamide prodrugs prepared as described herein are tested using crude mycobacterial extracts. Cleavage of the pyrazinamide analogs to pyrazinoic acid is analyzed by reverse phase high-performance liquid chromatography. Pyrazinoic acid is isolated by acid extraction, using either perchloric acid or trifluoroacetic acid. Acid soluble materials are then precipitated by centrifugation, and the acid extract neutralized with sodium bicarbonate. Pyrazinoic acid content is determined by HPLC using a C-18 column and a gradient of methanol or acetonitrile and water, and pyrazinoic acid quantitated by absorbance at 249 nanometers (the absorbance maximum for pyrazinoic acid).

Non-specific, non-mycobacterial hydrolysis of the pyrazinamide prodrugs of the invention is assayed using a commercially-available (Pel-Freeze, Rogers, Ariz.), crude ammonium sulfate fractionated rat liver extract (Mackall et al., 1979, *Analyt. Biochem.* 95: 270–274).

EXAMPLE 3

Establishing Macrophage Cultures and Infecting Macrophages with *M. fortuitum* and *M. chelonei*

In order to assay the capacity of infected macrophages to specifically cleave pyrazinoic acid conjugates of the invention, in vitro macrophage cell cultures are developed and infected with the non-pathogenic mycobacteria strains *M. fortuitum* and *M. chelonei*, and then used to determine if the infected macrophages selectively release fluorescent compounds conjugated with secondary amides.

a. Mouse Macrophage Cell Cultures.

Cell cultures are established from either (i) bone-marrow derived macrophages from C57/BL6 mice (H-2b), or (ii) transformed monocyte/macrophage isolated from C57/BL6 mice or BALB/c mice sources. 10–12 week old female mice, purchased from Bantin-Kingman (Seattle, Wash.) are used for these experiments. Mice are housed in plastic micro-isolater cages in a temperature- and humidity-controlled environment with a 12 hour light/dark cycle and fed Purina Lab Chow and water ad libitum. Cages, bedding, and food are autoclaved prior to use and all cage changes and mice handling are performed in laminar air-flow hoods. All mice are quarantined for a minimum of one week before experimental use.

b. Preparing the Cell Cultures Monolayers.

Bone marrow derived macrophages (BMMF) from C57/BL6 mice (MHC haplotype $H-2^b$) and a monocyte/macrophage cell line (J774A.1; MHC haplotype $H-2^d$, ATCC, Manassas, Va.) are used for these studies. These cell types permit investigation of the efficacy of the dye-linked microparticles drug-delivery system in both primary cell culture isolates as well as transformed cell lines. In addition, inbred C57/B16 and BALB/c mice exhibit the $Bcg^S$ phenotype that is more permissive relative to infection with saprophytic and rapidly-growing mycobacteria such as *M. chelonei*, and *M. fortuitum* (Denis et al., 1990, *J. Leuk. Biol.* 47: 25–29; Radzioch et al., 1991, *J. Leuk. Biol.* 50: 263; van Furth, 1990, *Res. Microbiol.* 141: 256; Nibbering et al., 1994, *Scand. J. Immunol.* 40: 187).

BMMF cell cultures are established by collecting bone marrow cells from the long bones from the hind limbs of donor mice and culturing these cells in 24-well tissue culture plates at $5-10 \times 10^5$ cells/mL/well in DMEM culture medium supplemented with 10% FCS, 30% supernatant from L929 cells (a source GM-CSF-1; L cells are cultured in DMEM with 5% FCS) and antibiotics (100 U/mL penicillin and 100 mg/mL streptomycin sulfate). After 6–8 days at 37° C. and 6–7% $CO_2$, established BMMF monolayers are washed with DMEM and recultured in 10% FCS/DMEM without antibiotics for an additional 24 hours. Thereafter, BMMF monolayers are infected with viable *M. fortuitum* or *M. chelonei* as described below.

J774.1 cell cultures are plated in 24-well tissue culture plates using $2.5 \times 10^5$ cells/mL/well in 5% FCS/DMEM with antibiotics (penicillin and streptomycin). After 18–20 hours at 37° C. and 6–7% CO, J774.1 monolayers are washed three time with DMEM and recultured in fresh 5% FCS/DMEM without antibiotics, and immediately infected with viable *M. fortuitum* or *M. chelonei* as described below.

c. Infection of Cell Monolayers.

BMMF and J774.1 cell monolayers are infected with viable *M. fortuitum* or *M. chelonei*. These mycobacterial species were chosen for these studies because (1) they exhibit more rapid in vitro intracellular growth than other mycobacteria (Denis et al., 1990, ibid.; Radzioch et al., 1991, ibid.; van Furth, 1990, ibid.; Nibbering et al., 1994, ibid.), and (2) they are opportunistic pathogens for mammals (Steven et al., 1992, *Cornea* 11: 500; Sing et al., 1992, *Tubercle & Lung Dis.* 73: 305) and therefore represent appropriate models for more pathogenic mycobacteria.

*M. fortuitum* and *M. chelonei* are cultured in Middlebrook 7H9 liquid broth to midlog phase (3–4 days) and aliquots frozen at –80° C. Frozen aliquots are thawed and CFU titers determined by plating serial dilutions (in sterile PBS with 0.1% Tween 80) onto Middlebrook 7H11 plates. The optimal multiplicity of infection (MOI) for the cell monolayers is determined in preliminary experiments, with mycobacteria added in 0.5 mL of 5–10% FCS/DMEM (without antibiotics). The optimal MOI is indicated by the maximal differential in mycobacterial CFU between 1 and 48 hours following infection, as this differential enhances the ability to detect urease activity.

Six hours following infection, cell monolayers are washed three times with warm DMEM (to remove extracellular bacteria) and recultured at 37° C. and 6–7% $CO_2$ in 5–10% FCS/DMEM without antibiotics, or with gentamicin sulfate to inhibit growth of extracellular mycobacteria. This in vitro infection methodology has been successfully demonstrated in preliminary experiments with slower growing mycobacteria. Although *M. fortuitum* and *M. chelonei* are rapidly growing mycobacterium, they still grow more slowly than most common bacteria. Therefore, a 24–48 hour period of infection for macrophage cell monolayers is required. Optimal in vitro infection of macrophages (of the Bcg[S] phenotype) with *M. fortuitum* or *M. chelonei* permits a 6-fold increase in intracellular mycobacteria at 24–48 hours following infection. Therefore, contacting infected cell with fluorescent dye-linked secondary pyrazinamide according to the invention at 12–18 hours after infection should provide sufficient numbers of infected macrophages as well as sufficient time for production of the mycobacterial enzyme by the intracellular mycobacteria, both of which represent essential elements in evaluating this drug-delivery system.

EXAMPLE 4

Measuring Release of Fluorescent Dye in Mycobacteria-infected Macrophage Cell Cultures The functional competence of *M. fortuitum*- and *M. chelonei*-infected macrophages to selectively release fluorescent dye from a fluorescent dye-linked secondary pyrazinamide is determines as follows.

1. Incubation of Infected Macrophage Cultures with Fluorescent-Dye-Linked Microparticles.

Mouse bone-marrow derived macrophages or J774 cells are infected with *M. fortuitum* or *M. chelonei* as described above. Purified infected macrophage cells are incubated with a fluorescent dye-linked secondary pyrazinamide of the invention at a concentration sufficient for fluorescence to be detected Uptake of the fluorescent dye-linked secondary pyrazinamide is determined by lysing a known number of macrophage cells and determining the accumulated dye fluorescence in solution. The effect of fluorescent dye-linked secondary pyrazinamide uptake on functional competence of non-infected macrophages is determined by comparing the bactericidal capacity of contacted and uncontacted cell populations against subsequent infection with the intracellular bacterial pathogen *Listeria monocytogenes* (Peck, 1985, *J. Immunol. Methods* 82: 131–140; Drevets and Campbell, 1991, *Infect. Immun.* 59: 517–523; Drevets et al., 1992, *J. Leuk. Biol.* 52: 70–79; Barry et al., 1992, *Infect. Immun.* 60: 1625–1632)

2. Pulsing Infected Cells with Fluorescent Dye-Linked Secondary Pyrazinamide and Determination of Enzyme Activity.

At 12–18 hours following infection of cell monolayers, cells are incubated with a bolus of fluorescent dye-linked secondary pyrazinamide, most preferably imbedded in a porous microparticle coated with a non-specifically degraded coating material (as disclosed, for4 example, in U.S. Pat. No. 6,063,759, incorporated by reference herein). The optimal concentration of the fluorescent dye-linked secondary pyrazinamide is determined as described in Example 3. At 2 hours after pulsing with the fluorescent dye-linked secondary pyrazinamide, cell monolayers are washed twice with warm DMEM and recultured at 37° C. and 6–7% $CO_2$ in 5–10% FCS/DMEM without antibiotics. At 6, 12, and 24 hours following addition of the fluorescent dye-linked secondary pyrazinamide, monolayer cells are lysed, either hypotonically with sterile water or with detergent (2.5% saponin or 0.1% NP-40; the quenching effects of detergents on fluorescence detection are evaluated prior to these studies). Cell supernatants from the lysed monolayers are clarified by centrifugation (10,000×g, 10 min) in microcentrifuge tubes equipped with 30 kilodalton molecular weight cut-off membranes. The relative fluorescence (as a measure of mycobacterial enzyme activity) of the supernatants from these centrifugations is determined by fluorescence spectrophotometry. Negative controls for these experiments consist of non-infected cell monolayers contacted with fluorescent dye-linked secondary pyrazinamide and infected cell monolayers not contacted with the fluorescent dye-linked secondary pyrazinamide.

It should be understood that the foregoing disclosure emphasizes certain specific embodiments of the invention and that all modifications or alternatives equivalent thereto are within the spirit and scope of the invention as set forth in the appended claims.

What is claimed is:

1. An antimycobacterial compound that is an inhibitor of a mycobacterium-specific enzyme, wherein the compound has the formula:

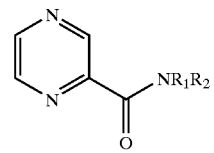

$R_1$ and $R_2$ can each independently be H, lower alkyl ($C_1$ to $C_{10}$), alkoxy, lower alkyl carboxy, β-lactam, or D- or L-amino acids, or di- or tripeptides, provided that at least one of $R^1$ and $R^2$ are not H.

2. The compound of claim 1 wherein $R_1$ and $R_2$ is methyl.

3. The compound of claim 1 wherein $R_1$ and $R_2$ is ethyl.

4. The compound of claim 1 wherein $R_1$ and $R_2$ is methoxy.

5. The compound of claim 1 wherein $R_1$ and $R_2$ is ethoxy.

6. The compound of claim 1 wherein $R_1$ and $R_2$ is carboxymethyl.

7. A pharmaceutical composition comprising the compound of claim 1, 2, 3, 4, 5 or 6 and a pharmaceutically acceptable carrier.

8. A method of treating an animal infected with a disease-causing microorganism of a Mycobacterium species, the method comprising the step of administering to the animal a therapeutically effective amount of a pharmaceutical composition of claim 7.

9. A method of killing a microorganism infecting a mammalian cell, the method comprising contacting said cell with the composition of claim 7.

10. A method of killing a tuberculosis-causing microorganism infecting a mammalian cell, the method comprising contacting said cell with the composition of claim 7.

11. The compound of claim 1 wherein $R_1$ or $R_2$ is β-lactam.

12. The compound of claim 1 wherein $R_1$ or $R_2$ is methyl.

13. The compound of claim 1 wherein $R_1$ or $R_2$ is ethyl.

14. The compound of claim 1 wherein $R_1$ or $R_2$ is methoxy.

15. The compound of claim 1 wherein $R_1$ or $R_2$ is ethoxy.

16. The compound of claim 1 wherein $R_1$ or $R_2$ is carboxymethyl.

* * * * *